US012502513B2

(12) United States Patent
Chun et al.

(10) Patent No.: US 12,502,513 B2
(45) **Date of Patent: *Dec. 23, 2025**

(54) VENTRICULOAMNIOTIC SHUNT FOR FETAL AQUEDUCTAL STENOSIS

(71) Applicant: UNIVERSITY OF PITTSBURGH—OF THE COMMONWEALTH SYSTEM OF HIGHER EDUCATION, Pittsburgh, PA (US)

(72) Inventors: Young Jae Chun, Wexford, PA (US); Stephen P. Emery, Pittsburgh, PA (US); Stephanie Greene, Glenshaw, PA (US); Joseph Raffael Sukinik, Rockville, MD (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 630 days.

This patent is subject to a terminal disclaimer.

(21) Appl. No.: 17/611,606

(22) PCT Filed: May 29, 2020

(86) PCT No.: PCT/US2020/035072

§ 371 (c)(1), (2) Date: Nov. 16, 2021

(87) PCT Pub. No.: WO2020/243394

PCT Pub. Date: Dec. 3, 2020

(65) Prior Publication Data

US 2022/0241566 A1 Aug. 4, 2022

Related U.S. Application Data

(60) Provisional application No. 62/853,778, filed on May 29, 2019.

(51) Int. Cl.
*A61M 27/00* (2006.01)
*B05D 1/18* (2006.01)

(52) U.S. Cl.
CPC ............. *A61M 27/006* (2013.01); *B05D 1/18* (2013.01); *A61M 2205/0266* (2013.01); *A61M 2207/00* (2013.01)

(58) Field of Classification Search
CPC ........ A61M 27/006; A61M 2205/0266; A61M 2207/00; A61M 2039/242; A61M 2039/244; A61M 2205/3344; B05D 1/18
See application file for complete search history.

(56) References Cited

U.S. PATENT DOCUMENTS 4,475,898 A * 10/1984 Brodner ............. A61M 25/007 604/9
4,955,862 A 9/1990 Sepetka
(Continued)

OTHER PUBLICATIONS

International Search Report and Written Opinion Issued in PCT/US2020/035072, Mailed on Aug. 12, 2020.

*Primary Examiner* — Philip R Wiest
*Assistant Examiner* — Matthew Wrubleski
(74) *Attorney, Agent, or Firm* — Carol A. Marmo; Eckert Seamans Cherin & Mellott, LLC

(57) ABSTRACT

The invention relates to an in-utero ventriculoamniotic shunting device that includes a composite shunt tube composed of polymer material, e.g., silicone-based material, and metallic wire, having a bend or curve formed in the length of the shunt tube, with one or more anchors composed of super-elastic wire or mesh, e.g., shape memory alloy wire or mesh structures, attached to the shunt tube, and a one-way passive valve composed of a thin polymer membrane. The anchors are effective to prevent migration and dislodgement of the shunting device following its deployment, and the valve is effective to prevent the backflow of amniotic fluid.

18 Claims, 7 Drawing Sheets

(56) References Cited

U.S. PATENT DOCUMENTS

| | | | | |
|---|---|---|---|---|
| 5,385,541 | A * | 1/1995 | Kirsch ................... | A61B 18/24 604/9 |
| 7,709,046 | B1 * | 5/2010 | Sahatjian ................. | B05D 7/52 427/535 |
| 2003/0018318 | A1 | 1/2003 | Melsky | |
| 2016/0136398 | A1 * | 5/2016 | Heilman ........... | A61M 25/0108 604/9 |
| 2018/0125707 | A1 * | 5/2018 | Khaderi .............. | A61M 27/006 |
| 2018/0296810 | A1 * | 10/2018 | Chen ..................... | A61M 25/00 |

* cited by examiner

VENTRICULOAMNIOTIC SHUNT FOR FETAL AQUEDUCTAL STENOSIS

CROSS-REFERENCE TO RELATED APPLICATION

This application is a U.S. National Stage Application under 35 U.S.C. § 371 of International Patent Application No. PCT/US2020/035072, filed on May 29, 2020, entitled "VENTRICULOAMNIOTIC SHUNT FOR FETAL AQUEDUCTAL STENOSIS", which claims priority under 35 U.S.C. § 119 (e) to U.S. Provisional Patent Application Ser. No. 62/853,778, filed May 29, 2019, entitled "VENTRICULOMANIOTIC SHUNT FOR FETAL AQUEDUCTAL STENOSIS", which are herein incorporated by reference.

FIELD OF THE INVENTION

The invention relates to a ventriculoamniotic device, e.g., shunt, for in-utero implantation to treat fetal aqueductal stenosis.

BACKGROUND

Severe fetal central nervous system (CNS) ventriculomegaly is a relatively common prenatal diagnosis, and it is known that fetal pressure hydrocephalus causes damage to the developing brain of a fetus or newborn. Hydrocephalus is defined as a clinical entity in which a disturbance of cerebrospinal fluid (CSF) circulation causes the accumulation of intraventricular CSF, resulting in progressive ventricular dilation. It can be divided as two groups: hydrocephalus seen in early life and hydrocephalus seen in adults based on the time of onset. In the early life hydrocephalus group, fetal hydrocephalus is of significant concern since children with an obvious prenatal onset of hydrocephalus have been found to be at high risk for early death or multiple neurological impairments. It is reported that fetal hydrocephalus occurs at an estimated rate of 0.2-1 per 1,000 deliveries, and the prevalence varies due to the various or obscure definitions of congenital hydrocephalus. Fetal pressure hydrocephalus, due to obstruction of flow of fluid through and then out of the ventricular system, damages the developing brain. Neurologic consequences are devastating and permanent.

In general, severe CNS ventriculomegaly is associated with poor neurologic outcomes. Severe ventriculomegaly is often secondary to an underlying malformation, deformation or disruption of brain parenchyma, and the prognosis may be associated with the primary diagnosis such as hydranencephaly, schizencephaly, or Dandy-Walker malformation. Whereas, aqueductal stenosis (AS) results in non-communicating hydrocephalus in an otherwise normally developing brain. AS is a unique neurodevelopmental anomaly that causes pressure hydrocephalus by obstruction of the aqueduct of Sylvius, which is the narrowest portion of the CNS ventricular system between the third and fourth ventricles, and may benefit from in-utero shunting. Stenosis of the aqueduct of Sylvius results in pathologic accumulation of cerebrospinal fluid within the lateral and third ventricles. Since CSF is continually produced by the choroid plexus but cannot exit the ventricular system, the fluid accumulates under pressure (supratentorial intracranial hypertension). Increased intracranial pressure results in compression of the cortical mantle, decreased vascular perfusion, and subsequent tissue ischemia. Additionally, expansion of the ventricular system causes distention of the brain tissue and mechanical axonal shear. Typical neurologic sequelae include blindness, hypothalamic dysfunction, seizures, developmental delay, and spasticity.

Traditionally, the term "ventriculomegaly" is used in prenatal diagnosis to describe the dilated lateral ventricles. Measurement of the atria of the lateral ventricle is standardized and reproducible. It is fundamentally different from other causes of hydrocephalus that result from a malformation, deformation, or disruption of the developing brain. Ventriculomegaly has been categorized as mild (10-15 mm) and severe (≥15 mm), or mild (10-12 mm), moderate (13-15 mm) and severe (≥16 mm). Ventriculomegaly is a nonspecific descriptive finding and is usually the consequence of an underlying process of either an imbalance of CSF production and absorption (communicating and obstructive hydrocephalus), or CSF that occupies the space where brain tissue does not (i.e., infectious or ischemic insults, malformations). Hydrocephalus implies increased intracranial pressure, which is a clinical diagnosis based on history and physical examination that, heretofore, could not be diagnosed in the fetus.

The prenatal diagnosis of fetal AS (FAS) is often suspected at the time of the anatomic survey ultrasound at 18-22 weeks gestation. Unlike ventriculomegaly from a malformation or disruptive processes, which can have the appearance of scant brain parenchyma, the ventriculomegaly from FAS has the appearance of overabundant CSF wherein the ventricular system is inflated, the lateral ventricles are enlarged both anteriorly and posteriorly, and brain parenchyma appears to be compressed against the calvarium. FAS is multifactorial in etiology, with acquired causes resulting in intrinsic obstruction being more common prenatally. These include obstruction to the aqueduct secondary to infection or intraventricular hemorrhage, or an aqueductal web. Extrinsic compression causes include tectal plate mass/thickening, tectal plate dysplasia or periaqueductal vascular malformation. In the case of progressive obstructive hydrocephalus from FAS, serial ultrasounds will likely demonstrate worsening hydrocephalus and distortion of intracranial anatomy. Fetuses with AS, usually have otherwise normal brains. Neurologic injury in AS is the result of pressure on the developing neurons. It therefore stands to reason that fetuses with AS may benefit from decompression of the ventricular system, thereby arresting brain injury and preventing ongoing damage. The timing of the diagnosis of FAS will be critical since successful prenatal intervention will need to be completed before irreversible neurologic damage occurs.

Fetal MRI has the ability to diagnose rhomboencephalosynapsis and dystroglycanoppathy-related cerebellar dysplasia. Ventriculomegaly in the setting of these anomalies is highly likely to be related to FAS. It may be that fetuses who are candidates for postnatal shunting will be candidates for prenatal shunting since the neurologic injury caused by AS will compound that of a neuronal migration disorder. MRI is also helpful in excluding other intracranial malformations, deformation or disruptive processes such as hydranencephaly and holoprosencephaly that can result in severe ventriculomegaly but would not benefit from in-utero shunting.

In-utero shunting of CSF from the ventricles to the amniotic fluid was attempted in the 1980s with the expectation of improving neurologic and pregnancy outcomes, but was abandoned due to a perceived lack of effect that was likely due to technological limitations at the time. The ventriculoamniotic shunts were, in general, simple silastic tubes with a one-way valve to prevent amniotic fluid from refluxing into the ventricles. They were placed by ultrasound guidance through a large bore needle. They had a tendency to clog and additionally, migrate since there was no effective means for anchoring the device to prevent dislodgement. Intrauterine treatment was shown to be technically feasible. However, shunting was abandoned in the mid-1980s due to a perceived lack of effect. In retrospect, the lack of effect was likely due to poor patient selection and technical difficulties as a consequence of technological limitations at the time. Because of the inability to accurately assess fetal neuroanatomy in the 1980s, shunts were placed in fetuses with lesions other than AS. Not surprisingly, analysis of the data on pregnancy outcomes after shunting showed no clear benefit. A moratorium was placed on fetal ventriculoamniotic shunting in the mid-1980s and since, there has been almost no progress in treatment of fetal hydrocephalus and ventriculoamniotic shunts are not commercially available. Also, there has been no significant progress made in the last few decades on the antenatal management of severe ventriculomegaly.

Prenatal ventricular decompression is currently not a management option for fetal pressure hydrocephalus. Current management for fetal hydrocephalus involves either preterm delivery followed by postnatal shunting or expectant management to term and then shunting. Problems associated with early delivery are concomitant prematurity, poor surgical candidacy, and a greater rate of shunt complications. Problems associated with expectant management are ongoing brain injury and obstetric complications related to macrocephaly (excessively large fetal head), which can impact the current as well as future pregnancies due to the need for cesarean delivery. The type of cesarean section typically required is a "classical," or vertical uterine incision which is subject to rupture in subsequent pregnancies, placing both mother and fetus at risk for death or disability. This represents an unfavorable risk-benefit assessment as the mother is exposed to significant risk, but the newborn may not receive benefit since neurologic damage is typically complete by term.

Thus, there is a need to address these issues and provide a multidisciplinary, evidence-based reassessment of ventriculoamniotic shunting for isolated FAS, which is the unique form of severe ventriculomegaly. An accurate diagnosis of FAS should precede utero intervention. It is expected that MRI will be an excellent adjunct to high-resolution prenatal ultrasound and next-generation genetic testing to correctly diagnose fetal AS in a timely manner while excluding other intracranial and extracranial anomalies.

Accordingly, the inventors have found that the use of state of the art prenatal diagnostics and superior shunt design provide improved apparatus and methods for ventriculoamniotic shunting for FAS. The invention addresses the aforementioned issues by identifying an appropriate patient population for ventriculoamniotic shunting, i.e., isolated AS, through prenatal detection devices and methods including ultrasound and MRI techniques and, designing and developing in-utero shunting devices and methods for arresting brain injury and allowing the pregnancy to proceed to term, after which standard ventriculoperitoneal shunting is performed in the newborn period. Neurologic function is potentially preserved while the pregnancy progresses to term. Term newborns are superior surgical candidates as compared to preterm infants.

SUMMARY OF THE INVENTION

The invention provides an in-utero ventriculoamniotic shunting device that includes a shunt tube, one or more anchors and a one-way passive valve.

In one aspect, the invention provides an in-utero ventriculoamniotic shunting device that includes a shunt tube including an exterior surface; an interior surface that forms a cavity; a first end; an opposite second end; a length extending between the first and second ends; a bend located in the length; an inner diameter; an outer diameter; and a composite that forms the inner diameter and the outer diameter including metallic wire and one or more silicone-based layers applied to the metallic wire; and one or more self-expanding anchors formed on the exterior surface along the length of the shunt tube, including a shape memory alloy wire or mesh structure; and a one-way passive valve positioned in the cavity of the shunt tube.

The metallic wire may include an elastic material such as nitinol. The metallic wire may be formed in a helical shape having a plurality of spirals.

The one or more self-expanding anchors can be composed of an elastic material such as nitinol. Further, the one or more anchors may include a cover composed of a material such as PTFE. The one or more anchors can be positioned at or near the first end or the second end of the shunt tube. In certain embodiments, the one or more anchors is located near or adjacent to the bend. The bend may be in the form of an elbow shape or angle from about 90 degrees to about 120 degrees. The one or more self-expanding anchors can be configured in the shape of two consecutive bulges or cages extending outwardly from the exterior surface of the shunt tube. In certain embodiments, one of the bulges or cages is located on a first leg adjacent the apex of the bend and the other of the bulges or cages is located on a second leg of the apex. One of the bulges or cages may be positioned on one side of the bend and the other of the bulges or cages is positioned on the opposite side of the bend.

The one or more anchors can be mechanically attached to the exterior surface of the shunt tube and extend outwardly therefrom.

The one-way passive valve may be located at one end or the opposite other end of the shunt tube. In certain embodiments, the valve is positioned in the cavity and in the region of the one or more anchors located on the exterior surface of the shunt tube. In certain embodiments, the one-way passive valve includes a membrane cover mechanically connected to a portion of the interior surface of the shunt tube in a hinge-like configuration.

The length of the shunt tube can be from about 2 to about 10 cm; the inner diameter from about 0.45 to about 0.8 mm; and the outer diameter from about 0.7 to about 1.5 mm.

In another aspect, the invention provides a method of ventriculoamniotic shunting in fetal isolated aqueductal stenosis. The method includes prenatally detecting and diagnosing aqueductal stenosis in a fetus; forming a shunting device including fabricating a shunt tube that includes an exterior surface; an interior surface; a cavity formed by the interior surface; a first end; an opposite second end; a length extending between the first and second ends; a bend positioned in the length; an inner diameter; an outer diameter; and a composite that forms the inner diameter and the outer diameter, that includes metallic wire; and one or more silicone-based layers applied to the metallic wire; attaching one or more self-expanding anchors to the length of the shunt tube; and positioning a one-way passive valve in the cavity of the shunt tube.

In certain embodiments, the attaching of the anchors includes fabricating a shape memory alloy wire or mesh structure, thermally configuring the shape memory alloy wire or mesh structure to expand outwardly from the exterior surface of the shunt tube for preventing migration of the shunting device, and employing a mechanism for connecting the shape memory alloy wire or mesh structure to the shunt tube The foregoing method can further include introducing the shunting device in-utero through a skull and into a brain of the fetus, such that the first end of the shunt tube is positioned in the skull and the opposite second end of the shunt tube is positioned in an amniotic sac outside the skull; allowing cerebrospinal fluid in the brain to flow into the first end and through the shunt tube; pushing outward the flow of cerebrospinal fluid through the one-way passive valve of the shunt tube; and discharging the cerebrospinal fluid through the opposite second end of the tube into the amniotic sac.

In yet another aspect, the invention provides a method of preparing a ventriculoamniotic shunting in fetal isolated aqueductal stenosis. The method includes pre-forming a metallic wire in a helical shape to form a helical-shaped wire; applying one or more silicone-based layers to the helical-shaped wire; forming a composite shunt tube comprising the helical-shaped wire, including an exterior surface; an interior surface; a cavity formed by the interior surface; a first end; an opposite second end; a length extending between the first and second ends; a bend positioned in the length; an inner diameter; and an outer diameter; flexing the composite shunt tube to form a bend in the length; attaching one or more self-expanding anchors along the length of the shunt tube; and positioning a one-way passive valve in the cavity of the shunt tube.

In certain embodiments, applying the one or more silicone-based layers to the coiled wire is conducted by dip coating and gravitational drying.

BRIEF DESCRIPTION OF DRAWINGS

A full understanding of the disclosed concept can be gained from the following description of the preferred embodiments when read in conjunction with the accompanying drawings, in which.

DETAILED DESCRIPTION OF THE PREFERRED EMBODIMENTS

Figure 1:
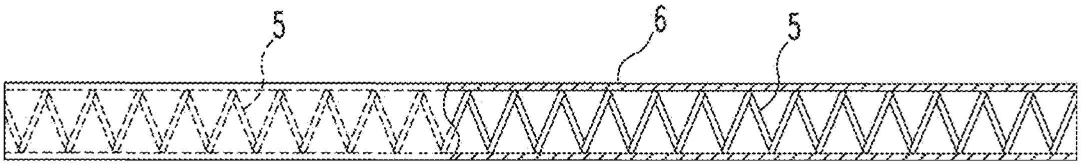
FIG. 1 is a schematic of a shunt tube having a helical-shaped wire within the tube, in accordance with certain embodiments of the invention.

The invention relates to devices and methods for identifying an appropriate patient population for in-utero ventriculoamniotic shunting, i.e., isolated AS, through detection devices and methods prenatally using both ultrasound and MRI techniques and, in-utero shunting devices and methods for arresting brain injury and allowing the pregnancy to proceed to term. The invention includes novel low-profile in-utero ventriculoamniotic shunting devices with one or more anchors and a one-way valve to relieve high intracranial pressure. The devices' functionality includes one or more of the following: relieving high intracranial pressure and, preventing device dislocation and inhibiting reflux of cerebrospinal fluid (CSF). The objectives of the devices and methods of the invention include one or more of arresting brain injury, preventing further damage, preserving neurologic function, and allowing for normal development thereby avoiding life-long suffering of affected children and the associated medical, emotional and financial burden of the disease.

The ventriculoamniotic shunting devices according to the invention have been designed and tested in-vitro and in-vivo, and found to achieve one or more of the following specific performance characteristics: percutaneous; ultrasound-guided placement; low-profile diameter to minimize the size of uterine and membrane puncture; an anchoring mechanism to prevent migration; a one-way valve to prevent influx of amniotic fluid into the ventricular system; sufficient compliance to prevent injury to intracranial or intra-amniotic structures without kinking or obstructing, and sufficient length and diameter to allow for CSF drainage while avoiding over-drainage.

In general, the ventriculoamniotic shunting devices are designed for percutaneous insertion to minimize maternal risk, and constructed of biomedical materials approved for human use by the Food and Drug Administration (FDA). Non-limiting examples of suitable materials include shape memory alloys that expand or contract as intended at body temperature and ultra-flexible thin polymeric membranes. A deployment device allows for standardization of insertion of the shunt.

In accordance with the invention, the ventriculoamniotic shunting devices, e.g., shunts, include a composite tube composed of a polymer material and ultra-thin metal wire. The shunt tube is composed of a soft material that is biocompatible, longitudinally flexible, as well as resistant to buckling and kinking. In certain embodiments, the tube is composed of silicone, e.g., a silicone-based material. Apparatus and techniques for forming the silicone tube are selected from a variety of fabrication apparatus and techniques known in the art, such as, dip coating the metal wire with the silicone-based material in a liquid form, and then using a gravitational drying process. The dimensions of the tube vary. In certain embodiments, the outer diameter is in a range from about 0.7 to about 1.5 mm or from about 0.8 to about 1.0 mm. The inside diameter is in a range from about 0.45 to about 0.80 mm or from about 0.50 to about 0.65 mm. The length of the tube also varies and in certain embodiments, is in a range from about 2 to about 10 cm or about 7 cm.

FIG. 1 shows schematically a ventriculoamniotic shunting device, in accordance with certain embodiments of the invention, including a composite tube 6 having a helical-shaped wire 5 in the length of the tube.

There are a variety of materials that are known for use as wire in constructing implantable biomedical devices, and are suitable for use in the invention. In certain embodiments, the metal wire of the shunt tube, e.g., silicone-based material, to form the composite tube includes a shape memory alloy, e.g., super-elastic material, such as nitinol (nickel-titanium alloy) wire. Nitinol is suitable for use in implantable biomedical devices because of its shape memory effect, super-elasticity and biocompatibility. The use of nitinol in a medical device allows for the efficient deployment in a less invasive procedure with its super-elastic attribute, e.g., super-elastic nitinol at body temperature allows for self-expanding deployment. Most vascular disease treatment procedures require instruments and devices that pass through very small openings and then elastically spring back into desired shapes. Nitinol clearly allows vast freedom in design as compared to other flexible materials. As for biocompatibility, it has been found in the art that almost no toxic effects or decrease in cell proliferation is associated with nitinol, as well as no inhibiting effect on the growth of cells in contact with its surface.

Non-limiting examples of suitable nitinol wire include cold-drawn super-elastic nitinol wire, which is commercially available from Confluent Medical, CA. The elastic moduli of this wire is in the range of 41 to 75 GPa with an ultimate tensile strength of 1070 MPa. The transformation temperature (i.e., Austenite finish temperature) is in a range between −25 and 30° C. The composition of nitinol wire includes about 55.8 wt. % of nickel and about 44.2 wt. % of titanium.

Figure 7:
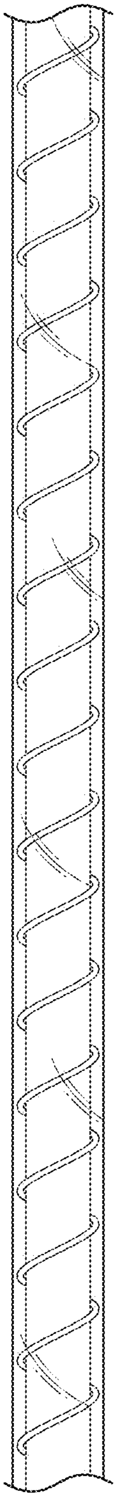
FIG. 7 is an image of a shunt device including a tube and a helical-shaped wire within the tube, in accordance with certain embodiments of the invention.

According to the composite shunt of the invention, the wire includes a helical shape or configuration, e.g., a spiral or coil, along the length of the silicone tube, e.g., tube wall, to form the composite tube. Various known apparatus and techniques are suitable for forming the tube. For example, the wire is formed into the helical shape, e.g., spiral or coil, and the biodegradable material for use in forming the tube, e.g., liquid silicone, is deposited or coated over the pre-formed helical-shaped wire, to form a coating or one or more layers on the wire, and cured. In certain embodiments, a dip coating with gravitational drying process is used to manufacture the composite shunt tube. The resultant tube includes the helical-shaped wire, with a coating or one or more layers of polymer material, e.g., silicone-based material, applied to its surface, such that the wire is inside or within the tube wall, e.g., embedded therein. FIG. 7 is an image that shows a composite shunt tube with a super-elastic nitinol helical coil wire structure therein, in accordance with the invention. In certain embodiments, the helical coil structure is produced by thermal shape-setting of super-elastic nitinol wire (s) that includes constraining the wire(s) into a shape using a mandrel, such as by wrapping the wire(s) around the mandrel, followed by a heat treatment. The dimensions of the wire(s) vary and include a diameter of about 0.005 inch (about 127 μm) or from about 0.002 to about 0.005 inch (about 76 to about 127 μm). Liquid silicone is applied to the helical structure and cured. The cure period varies and in certain embodiments, is about 12 hours. During the curing process, the mandrel is preferably fixed on the low-rpm motor (15 rpm) to obtain a composite tube having uniform wall thickness. The composite tube is then removed from the mandrel. The fabricated silicone-wire tube has a thickness from about 0.007 to about 0.009 inches.

The shunt also includes one or more self-expanding anchors. The one or more anchors are in the form of one or more thermal shape-set structures. Suitable materials for forming the anchor(s) include wire or tube constructed of a shape memory alloy, a super-elastic material, such as nitinol. In certain embodiments, the one or more anchors are composed of 30 to 100 μm-diameter nitinol wire or tube. The one or more anchors are mechanically attached to the exterior surface of the shunt tube and protrude or extend outwardly therefrom.

In certain embodiments, the anchor design includes the use of braided nitinol wires or micro laser-welded nitinol wires. In other embodiments, the anchor design includes use of a nitinol tube and a laser cutting process to fabricate a mesh structure.

One or more self-expanding anchors are attached or connected to the tube, e.g., the outer surface of the tube. After pre-shape setting of the wires, the anchor(s), e.g., the thermal shape-set structure(s), is mechanically attached or connected to the tube such as by micro-sutures or biocompatible polymer adhesives. The design of the anchor(s) varies and suitable designs include, but are not limited to, mesh and braided wire structures composed of nitinol. The length and diameter of the anchor(s) vary and in certain embodiments, are from about 1 to about 4 cm long and expandable to a diameter of about 2 to 3 mm. The anchor(s) is positioned along a portion of the length of the tube on the exterior surface.

Figure 2A:
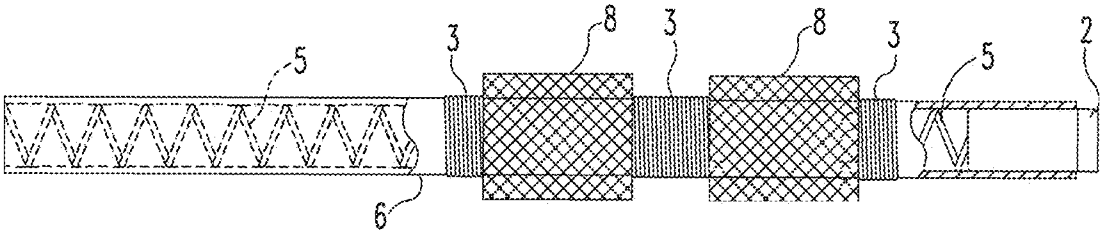
FIG. 2A is a schematic of the shunt tube shown in FIG. 1 including anchors, sutures to connect the anchors to the exterior surface of the tube and a one-way valve positioned within the tube, wherein the valve is in a closed configuration, in accordance with certain embodiments of the invention.

FIG. 2A schematically shows the composite tube in FIG. 1 including anchors 8 connected to the exterior surface of the tube 6 using sutures 3. FIG. 2A also shows a one-way valve 2, in a closed configuration, positioned inside of the tube 6.

In certain embodiments, one or more anchors are positioned in the region of, e.g., adjacent to or near, a bend that is located in the tube length. In other embodiments, one anchor is positioned at or near one end of the tube and optionally, another anchor is positioned at or near an opposite end of the tube.

In certain embodiments, the composite tube is flexed or bent such that there is a curve or bend formed within the length of the tube and one or more anchors are positioned on the bend, or near or adjacent to the bend. The selected position or region of the curve or bend along the length of the tube, and the degree of angle of the curve or bend varies. In certain embodiments, the curve or bend is positioned in the middle, e.g., at the midpoint, of the length of the shunt and in other embodiments, the curve or bend is positioned closer to one end of the length of the shunt tube. According to certain embodiments, the bend is in the form of an elbow shape or angle from about 90 degrees to about 120 degrees. The one or more anchors is positioned on, before and/or after the curve or bend region. In certain embodiments, the one or more anchors is located at the bend in the length of the tube. For example, the one or more anchors is located on the portion of the shunt tube that forms the bend, e.g., apex of the bend, or on a portion of the tube length that forms a first leg adjacent the apex of the bend and/or another anchor is located on a portion of the tube length that forms a second leg adjacent the apex. For instance, wherein the anchor includes two structures in series, e.g., a dumbbell shape, the bend, e.g., apex of the bend, is positioned in the middle or between the two structures.

Further, in accordance with the invention, the one or more anchors preferably include a cover composed of a material such as PTFE. In certain embodiments, the cover is attached or connected to the thermal shape-set structure, e.g., nitinol wire or tube structure.

In a non-limiting example, a pre-shaped nitinol anchor with two consecutive (in series) bulged structures having a closed-cell shape, are formed on the exterior surface of the tube length with the bend or curve, e.g., apex, positioned between them such that one bulged structure is located before the bend or curve (on one leg of the apex) and the other bulged structure is located after the bend or curve (on the other leg of the apex).

Figure 2B:
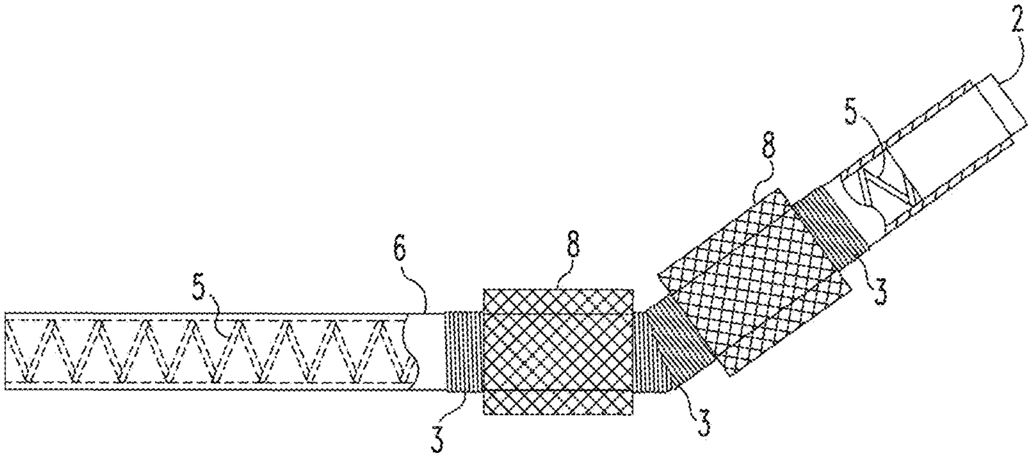
FIG. 2B is a schematic of the shunt tube shown in FIG. 2A including a bend in the shunt tube, in accordance with certain embodiments of the invention.

FIG. 2B schematically shows the shunt tube of FIG. 2A with a bend positioned between each of the anchors 8 with sutures 3 to connect the anchors 8 to the exterior surface of the tube 6.

In certain embodiments, the two consecutive (in series) bulged structures resemble a dumbbell or dual dumbbell shape. These structures are constructed of braided shape memory alloy wire, e.g., nitinol wire, or mesh, e.g., nitinol tube fabricated by laser cutting to form the mesh. The braided wire or mesh is coiled or wrapped around the outer surface of the composite tube to form the bulged structures thereon. The coiled or wrapped braided wire or mesh is attached or adhered to the outer surface of the composite tube using sutures or adhesive patches.

Figure 8:
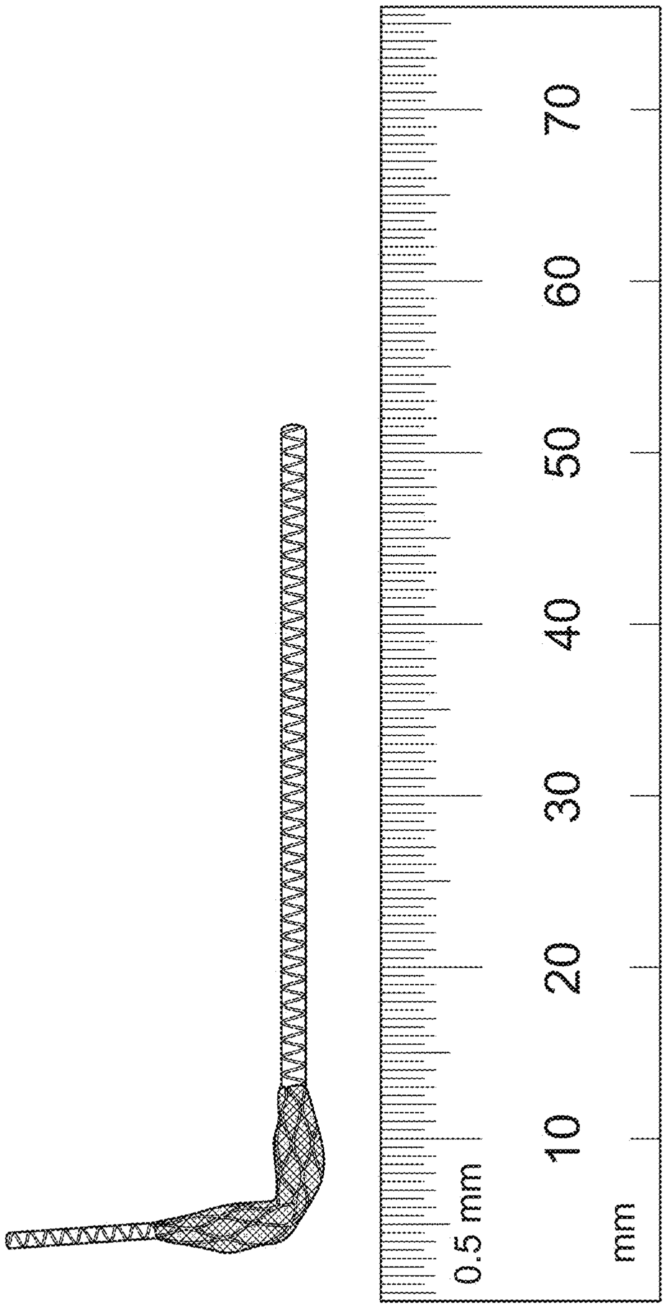
FIG. 8 is an image of a bent tube having anchors attached thereto for the shunt device, in accordance with certain embodiments of the invention.

FIG. 8 is an image that shows a suitable anchor design in accordance with certain embodiments of the invention. FIG. 8 includes a shunt tube with a helical coil structure embedded therein, and a wire anchor that is coiled around a bended portion (about a 90-degree bend in the middle of the anchor) of an outer surface of the tube. The anchor includes two braided or mesh bulged closed-cell structures, extending outwardly from the outer surface of the tube. The structures are composed of nitinol wire to maintain the shape. The nitinol wire is covered with thin PTFE, e.g., less than about 100 μm thickness. Typically, one end of the wire anchor includes a first suture and at another opposite end of the wire anchor is positioned a second suture, which are operable to connect/attach the wire anchor to the exterior surface of the tube. In certain embodiments, wherein the anchor includes two bulged structures in series, a third suture is positioned between the two bulged structures.

The diameter of the deployed anchor is about 2.8 mm. The height and length of each of the mesh or bulged structures varies. The tapered shape on both ends of the anchor allows for ease of delivery of the shunt device.

It is contemplated and understood that the design and shape of the one or more wire anchors vary widely and are not limited by the design and shape illustrated in FIG. 8. Generally, a variety of anchor designs or shapes are suitable for use provided that they preclude displacement of the tube when placed in-utero. Thus, suitable designs and shapes include those that are effective to prevent migration and dislodgement of the shunting device after its deployment.

In certain embodiments, forming a shunt device with a nitinol anchor includes the following: fabricating a helical-shaped, e.g., spiral or coil, shape memory alloy wire, e.g., nitinol, via a process of thermal shape setting of super-elastic nitinol wire; embedding the spiral nitinol wire in a silicone tube via a process of application or coating of the spiral nitinol wire with silicone; curing the silicone tube; integrating braided and/or mesh nitinol anchors on the tube using 7-11 size nylon sutures and/or biocompatible polymer adhesives; covering the anchors with a thin or ultra-thin ePTFE membrane to prevent any leakage of the fluid flow.

As aforementioned, nitinol wires or tubes are suitable for use in fabricating the anchors for the ventriculoamniotic shunt devices, in accordance with the invention. Nitinol is a common and well-known material widely used for implantable biomedical devices because of its shape memory effect, super-elasticity and biocompatibility, and the use of nitinol in a medical device allows for the efficient deployment in a less invasive procedure with its super-elastic attribute, e.g., super-elastic nitinol at body temperature allows for self-expanding deployment. Most vascular disease treatment procedures require instruments and devices that pass through very small openings and then elastically spring back into desired shapes. Nitinol clearly allows vast freedom in design as compared to other flexible materials. As for biocompatibility, it has been found in the art that almost no toxic effects or decrease in cell proliferation is associated with nitinol, as well as no inhibiting effect on the growth of cells in contact with its surface.

Non-limiting examples of suitable nitinol wire for fabricating the anchor(s) include cold-drawn super-elastic nitinol wire, which is commercially available from Confluent Medical, CA. The elastic moduli of this wire is in the range of 41 to 75 GPa with an ultimate tensile strength of 1070 MPa. The transformation temperature (i.e., Austenite finish temperature) is in a range between −25 and 30° C. The composition includes about 55.8 wt. % of nickel and about 44.2 wt. % of titanium. The nitinol wire anchor(s) is optionally covered to provide a continuous conduit for fluid flow. The cover material consists of thin film metallic or polymer layers, such as, thin layers of nitinol membrane, ePTFE, Dacron polyester, and mixtures and combinations thereof.

Figure 9:
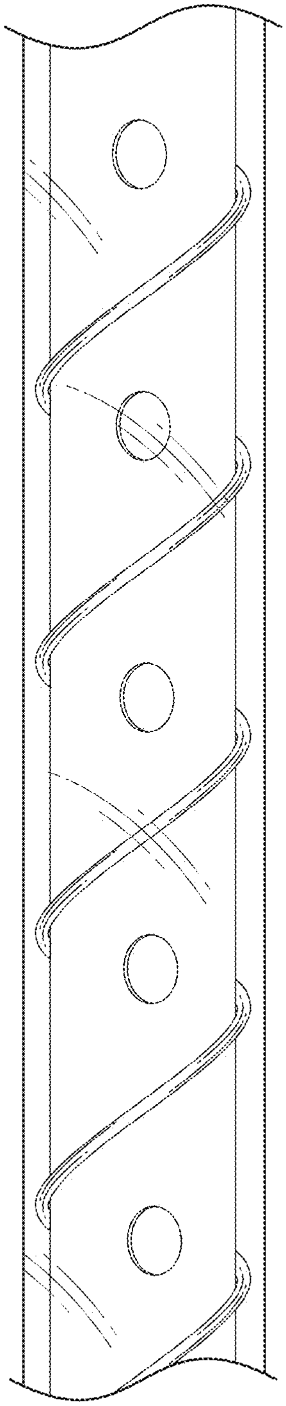
FIG. 9 is an image of the tube for the shunt device shown in FIG. 7 including holes created on the side of the tube, in accordance with certain embodiments of the invention.

FIG. 9 is an image that shows the tube for a shunt with a super-elastic nitinol helical coil wire structure therein, as shown in FIG. 7. FIG. 9 additionally shows holes on the side of the silicone tube, which were created or formed using a laser process. The presence of the holes increases the flexibility of the silicone tube. The size of each of the holes is about 200 micrometers. Further, as shown in FIG. 9, black debris was left around the holes. This debris is eliminated by use of ultrasonic cleaning apparatus and methods.

Additionally, a low-profile one-way valve is attached or connected to the shunt tube. The one-way valve is positioned inside the open cavity of the shunt tube, and attached or connected to the tube wall. The location of the one-way valve along the length of the shunt tube varies. In certain embodiments, the one-way valve is located at or near an end of the shunt tube.

Figure 3:
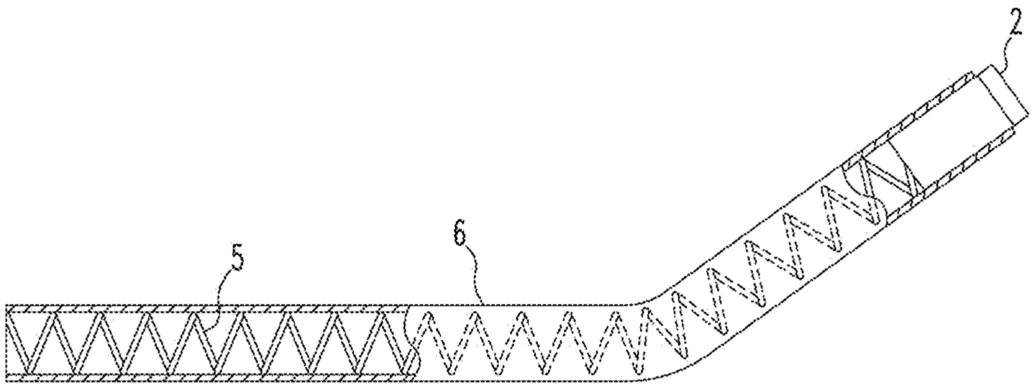
FIG. 3 is a schematic of the shunt tube shown in FIG. 1 including a one-way valve positioned inside the tube, wherein the valve is in a closed configuration, in accordance with certain embodiments of the invention.

FIG. 3 schematically shows a shunt tube in a bent configuration including a helical-shaped wire 5 within the tube 6 to form a composite, and a one-way valve 2 positioned inside an end of the tube 6, wherein the valve 2 is in a closed configuration.

Figure 4:
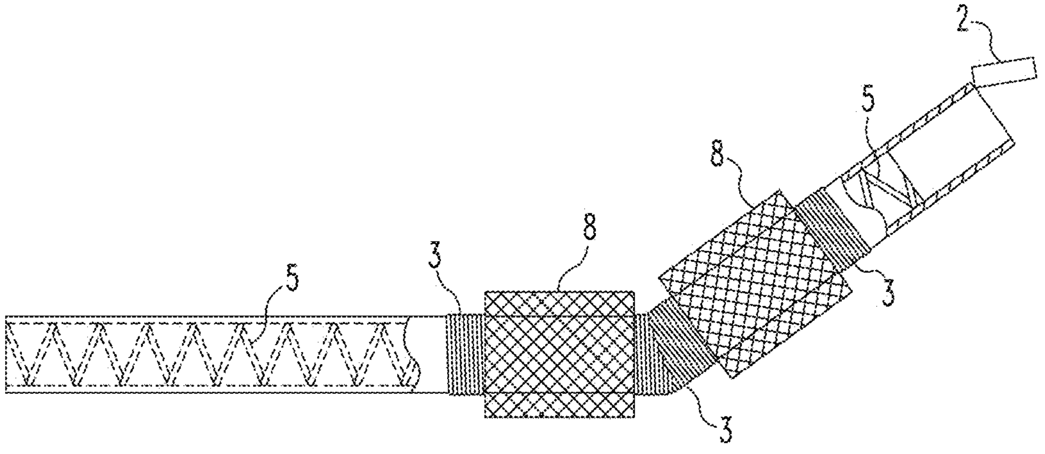
FIG. 4 is a schematic of the shunt tube shown in FIG. 3 including anchors, sutures to connect the anchors to the exterior surface of the tube and a one-way valve positioned within the tube, wherein the valve is in an open configuration, in accordance with certain embodiments of the invention.

FIG. 4 schematically shows the composite shunt tube of FIG. 3 including anchors 8 connected to the exterior of the tube 6 using sutures 3, wherein the valve 2 is in an open configuration.

In other embodiments, the one-way valve is located inside the shunt tube in the region where the anchor is attached to the outside of the shunt tube. The valve is mechanically attached or connected to the shunt tube, e.g., interior tubular wall or inner diameter, using micro-suturing or biocompatible polymer adhesives. The design and construction of the one-way valve varies. The valve is composed of various materials, such as, polymeric membrane, that is known in the art. Preferable materials include those that have a degree of elasticity (e.g., when used in accordance with the invention, capable of resisting forward and back flow). The elasticity of the material is a consideration because the device typically is partially attached, such as to function in a hinge-like manner without the use of an actual hinge. In certain embodiments, the material of construction of the one-way valve includes combinations of thin film nitinol and ePTFE. Further, in certain embodiments, the one-way valve includes a round disk shape, e.g., corresponding to the inner or outer tube diameter. The disk is composed of ePTFE with a thickness from about 100 to about 200 μm. Alternately, thin film nitinol with a thickness from about 5 to about 10 μm is used. Thin film nitinol is super-elastic at body temperature and therefore, allows the valve to open with pressurized fluid and close with its own elasticity to prevent back flow or reflux.

Figure 10:
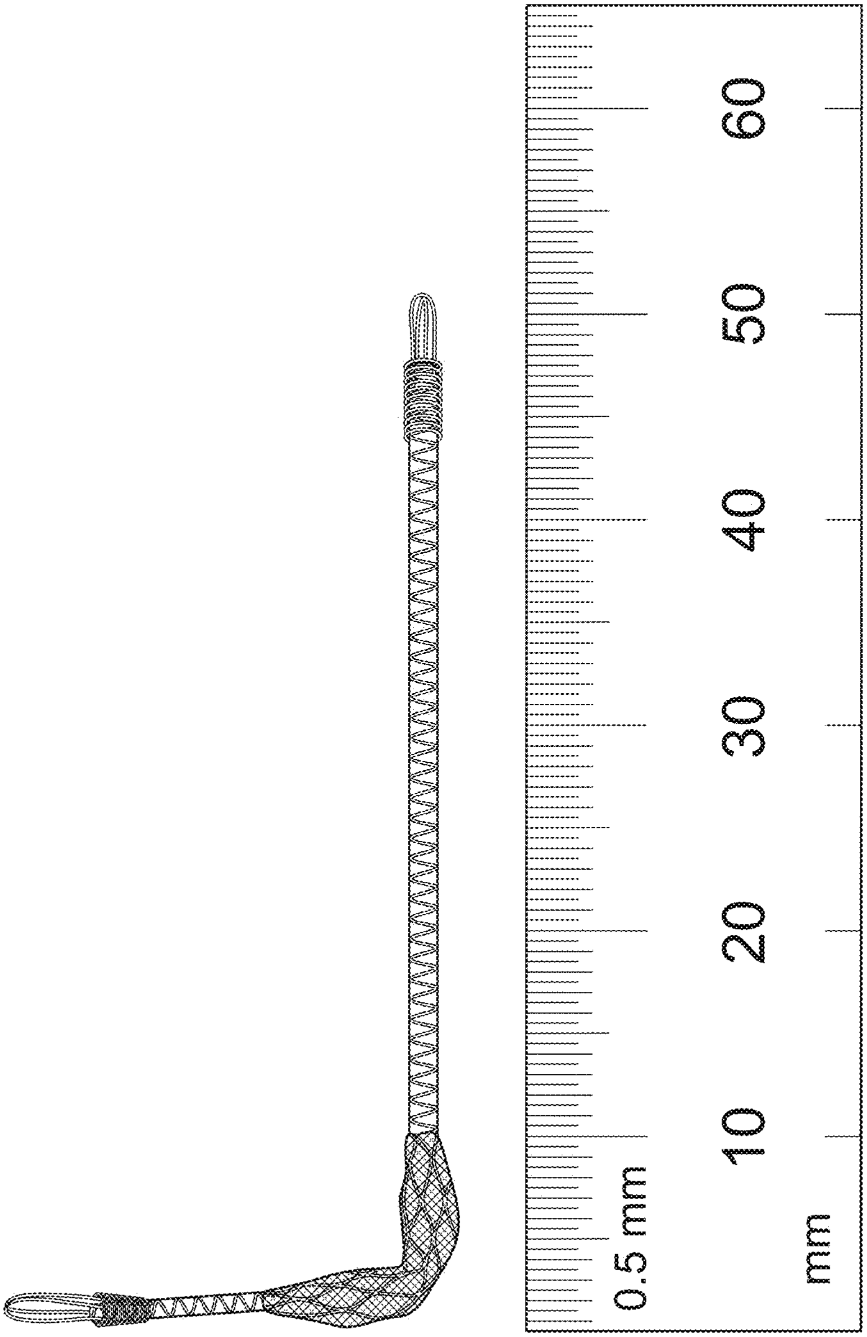
FIG. 10 is an image of the tube for the shunt device shown in FIG. 8 including a one-way valve on an end of the shunt device, in accordance with certain embodiments of the invention.

FIG. 10 is an image of a shunt device including a tube with a helical coil structure therein, and a wire anchor that is coiled around a bended portion (about a 90-degree bend in the middle of the anchor) of an outer surface of the tube, as shown in FIG. 8. Additionally, FIG. 10 includes two cages attached at both ends and a valve, e.g., a one-way valve, which is designed, manufactured and attached to an end of the tube to prevent any backflow of amniotic fluid into the fetal brain.

In certain embodiments, suitable one-way valves for use in the invention include biomimetic bi- or tri-leaflets (similar to cardiac or venous valves). The valve permits maximum fluid flow when opened, and provides a low-profile structure because of the use of thin elastic membranes. In certain embodiments, a simple, low-profile, one-way valve includes covering one end of the tube, e.g., catheter, with ePTFE membrane (about 200 μm thick). The membrane is attached along a portion of the perimeter of the tube end. The membrane is not attached along the entire perimeter of the tube end, such as not to completely seal the opening of the tube. Thus, the partial attachment along the perimeter provides for a hinge-like configuration, which automatically opens to allow fluid to flow out of the tube and automatically closes to preclude back flow into the tube.

In an embodiment of the invention, an ultra-compliant silicone composite tube having spiral or coil metallic wire embedded therein is used. In this embodiment, the tube has an outer diameter of about 1.0 mm and an inner diameter of about 0.6 mm. Two anchors are mechanically attached to the outer surface of the tube. Each of the anchors consists of a super-elastic 3 um-braided, laser-cut, or laser welded cylindrical nitinol wire structure. The two anchors are positioned substantially on or at a bend or curved portion in the length of the tube. As mentioned herein, in accordance with the invention, it is understood that various anchor designs are used.

In accordance with certain embodiments, the ventriculoamniotic shunt device is implanted in-utero in a brain of a fetus. The fetal skull houses the fetal brain. A catheter tube is introduced through the skull into the brain, such that one, e.g., proximate, end of the tube is positioned inside the skull and an opposite, e.g., distal, end of the tube is located outside the skull in the amniotic sac. The tube serves as a conduit to drain excessive CSF from the brain to the amniotic sac. The tube has two anchors, e.g., thermal-shaped nitinol wires, attached to an outer surface of the tube using sutures, to prevent dislocation of the tube. One anchor is positioned within the skull and the other anchor positioned outside of the skull. The proximate end of the tube, which is positioned within the skull and brain, is open to allow fluid to enter the proximate end of the tube and flow there through. The distal end of the tube, which is located outside of the skull, has a one-way valve partially affixed along a perimeter of the distal end of the tube. Thus, excessive CSF enters the proximate end, flows through the tube, pushes the valve into its open configuration, and exits into the amniotic sac. When there is no excessive CSF flowing through the tube, the valve is in its closed configuration to prevent reflux of CSF, such that only flow from the brain to the amniotic sac is allowed.

Figure 5:
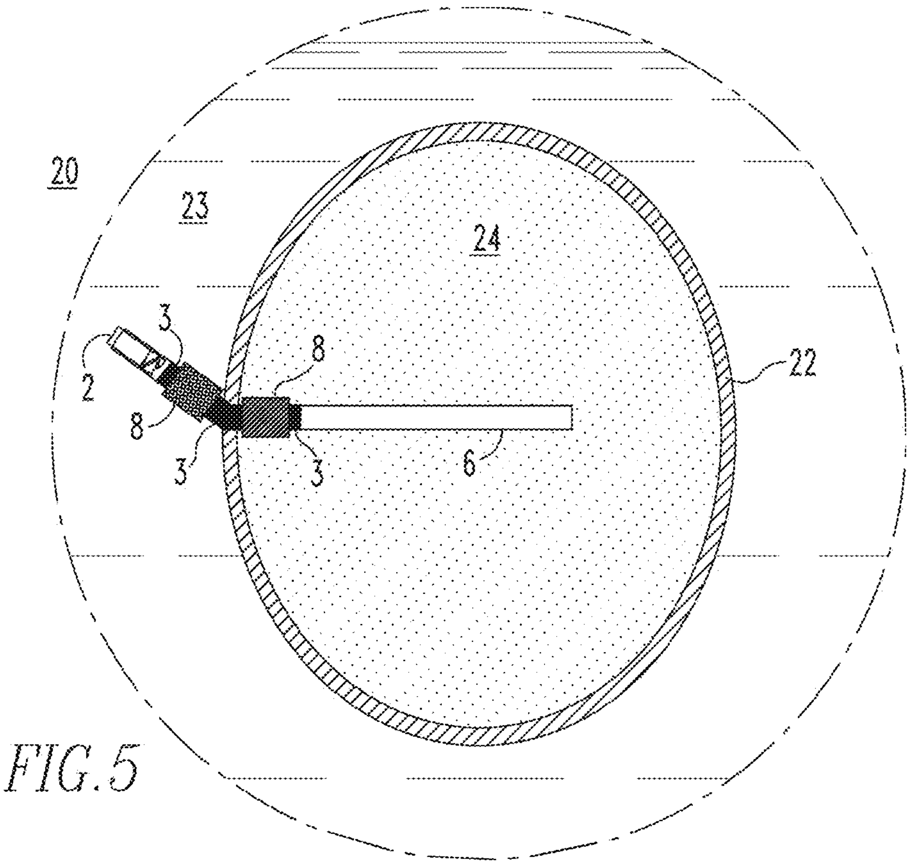
FIG. 5 is a schematic of the shunt tube shown in FIG. 2B positioned within the brain of a fetus, in accordance with certain embodiments of the invention.

FIG. 5 schematically shows a shunt system 20 according to certain embodiments of the invention that includes the tube 6 having a bent configuration with a helical-shaped wire in the tube 6 to form a composite structure, anchors 8 connected to the exterior of the tube 6 using sutures 3 and a one-way valve 2 positioned inside the tube at an end. The tube 6 is implanted in a fetal brain, in accordance with certain embodiments of the invention. FIG. 5 includes a fetal skull 22 that houses a fetal brain 24. The tube 6 is introduced through the skull 22 into the brain 24, such that one, e.g., proximate, end of the tube 6 is positioned inside the skull 22 and an opposite, e.g., distal, end of the tube 6 is located outside the skull 22 in the amniotic sac 23. The tube 6 serves as a conduit to drain excessive CSF from the brain 24 to the amniotic sac 23. The anchors 8 prevent dislocation of the tube 6. One anchor 8 is positioned within the skull 22 and the other anchor 8 is positioned outside of the skull 22. The proximate end of the tube 6 that is positioned within the skull 22 and brain 24, is open to allow fluid to enter the proximate end of the tube 6 and flow there through. The distal end of the tube 6 that is located outside of the skull 22, has the one-way valve 2 partially fixed along a perimeter of the distal end of the tube 6. Thus, excessive CSF enters the proximate end, flows through the tube 6, pushes the valve 2 into its open configuration, and exits into the amniotic sac 23. When there is no excessive CSF flowing through the tube 6, the valve 2 is in its closed configuration to prevent reflux of CSF, such that flow only from the brain 24 to the amniotic sac 23 is allowed.

Figure 6A:
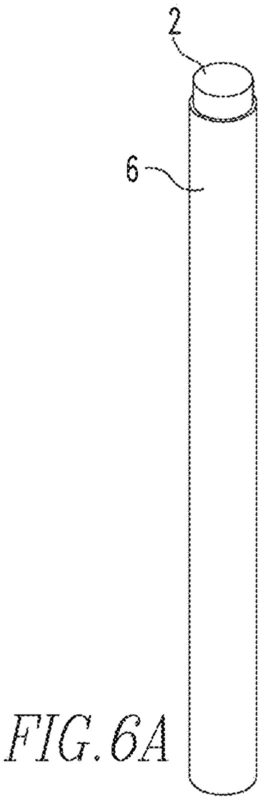
FIG. 6A is a schematic of the one-way valve in a closed position, in accordance with certain embodiments of the invention.
Figure 6B:
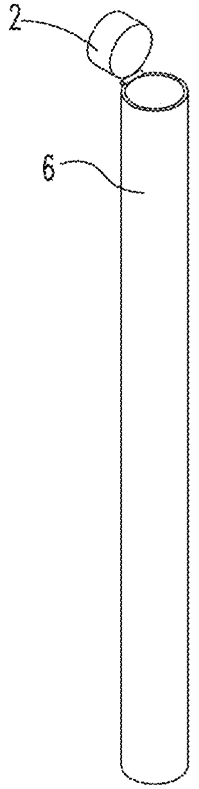
FIG. 6B is a schematic of the one-way valve in an open position, in accordance with certain embodiments of the invention.

FIGS. 6A and 6B schematically show detailed views of the valve 2. FIG. 6A illustrates the closed configuration of the valve 2, such that it covers the opening of the tube 6, and FIG. 6B illustrates the open configuration of the valve 2, such that it is pushed away from the tube 6 to partially expose the opening.

It is contemplated that ventriculoamniotic shunting devices designed and developed in accordance with the invention exhibit one or more of the following performance characteristics:

- Percutaneous, ultrasound-guided insertion technique to minimize maternal harm;
- Ability to anchor the shunting device to reduce potential for dislodgement;
- One-way valve mechanism to prevent reflux of amniotic fluid into the cerebral ventricles;
- Sufficiently large bore to prevent occlusion from clot or debris;
- Sufficiently small bore to prevent over-drainage of CSF;
- Capability for prolonged (e.g., about four months) drainage during fetal growth; and
- Composed of materials that are atraumatic to CNS structure (e.g., ependyma, white matter) internally and to membranes, placental vessels and myometrium externally for the duration of deployment.

In certain embodiments, the ventriculoamniotic shunting devices include a composite tube of silicone with a superelastic nitinol coil embedded within the silicone; a 90- to 120-degree bend in the curve; a dual dumbbell-like structure having two bulging closed-cell structures in series, constructed of braided nitinol wire or fabricated nitinol mesh with a PTFE cover; and a low-profile one-way valve constructed of ePTFE, electrospun polymer or thin film nitinol, attached to the inside of the composite tube in the anchor region along the length of the composite tube using microsuturing or biocompatible polymer adhesives.

Furthermore, it is contemplated that potential candidates for the ventriculoamniotic shunting devices exclude those fetuses with identified genetic anomalies that would preclude normal development with amnioscentesis.

It should be understood that the embodiments described herein and the example below are for illustrative purposes only and that various modifications or changes in light thereof will be suggested to persons skilled in the art and are to be included within the spirit and purview of this application.

Example

Fetal sheep were injected with BioGlue, a biological epoxy of purified bovine albumin and glutaraldehyde, into the cisterna magna at mid-gestation (80-90 days of 145 days gestation). The BioGlue remained within the cisterna magna and therefore, did not interfere with or obscure intraventricular histology. The shut device was placed at varying gestational ages between 110 and 130 days. Shunted brains were compared to non-shunted hydrocephalic controls at term. Using immunocytochemical staining, the hypothesis that neuronal injury in fetal hydrocephalus is secondary to increased intracranial pressure, which leads to tissue ischemia and mechanical axonal shear, was supported.

We claim:

1. An in-utero ventriculoamniotic shunting device, comprising:
- a shunt tube, comprising:
  - an exterior surface;
  - an interior surface;
  - a cavity formed by the interior surface;
  - a first end configured to be positioned inside a skull of a fetus;
  - an opposite second end configured to be positioned outside the skull of a fetus;
  - a length extending between the first and second ends;
  - at least two self-expanding anchors formed on the exterior surface along the length of the shunt tube, the at least two self-expanding anchors comprising a shape memory alloy wire or mesh structure, positioned in series, comprising:
    - a self-expanding first anchor configured to be positioned inside the skull of a fetus; and
    - a self-expanding second anchor configured to be positioned outside the skull of a fetus;
  - a bend in an elbow shape or angle from about 90 degrees to about 120 degrees forming an apex in the length of the shunt tube and the apex of the bend positioned between the first anchor and the second anchor;
  - an inner diameter;
  - an outer diameter; and
  - a composite that forms the inner diameter and the outer diameter, the composite comprising:
    - metallic wire; and
    - one or more silicone-based layers applied to the metallic wire; and
  - a one-way passive valve positioned in the cavity of the shunt tube.

2. The device of claim 1, wherein the metallic wire and the shape memory alloy wire or mesh structure each comprises nitinol.

3. The device of claim 1, wherein the at least two self-expanding anchors comprise a cover comprised of PTFE.

4. The device of claim 1, wherein the at least two self-expanding anchors comprises two consecutive bulges extending outwardly from the exterior surface in series along the length of the shunt tube.

5. The device of claim 4, wherein the one of the two consecutive bulges is located on a first leg adjacent an apex of the bend and the other of the two consecutive bulges is located on a second leg of said apex.

6. The device of claim 1, wherein the bend comprises an elbow shape having an angle from about 90 degrees to about 120 degrees.

7. The device of claim 1, wherein the metallic wire is configured in a helical shape having a plurality of spirals.

8. The device of claim 1, wherein the one-way passive valve comprises a membrane cover mechanically connected to a portion of the interior surface of the shunt tube in a hinge-like configuration.

9. The device of claim 1, wherein the one-way passive valve is positioned in the cavity in the region of the at least two anchors positioned on the exterior surface of the shunt tube.

10. The device of claim 1, wherein the inner diameter of the shunt tube is from about 0.45 to about 0.8 mm and the outer diameter of the shunt tube is from about 0.7 to about 1.5 mm.

11. A method of ventriculoamniotic shunting in fetal isolated aqueductal stenosis, comprising:
- prenatally detecting and diagnosing aqueductal stenosis in a fetus;
- forming a shunting device, comprising:
  - fabricating a shunt tube, comprising:
    - an exterior surface;
    - an interior surface;
    - a cavity formed by the interior surface;
    - a first end configured to be positioned inside a skull of a fetus;
    - an opposite second end configured to be positioned outside the skull of a fetus,
    - a length extending between the first and second ends;
    - at least two self-expanding anchors formed on the exterior surface along the length of the shunt tube, the at least two self-expanding anchors comprising a shape memory alloy wire or mesh structure, positioned in series, comprising:
    - a self-expanding first anchor configured to be positioned inside the skull of a fetus; and
    - a self-expanding second anchor configured to be positioned outside the skull of a fetus;
  - a bend in an elbow shape or angle from about 90 degrees to about 120 degrees forming an apex in length of the shunt tube and the apex of the bend positioned between the first anchor and the second anchor;
    - an inner diameter;

an outer diameter; and
a composite that forms the inner diameter and the outer diameter, the composite comprising:
metallic wire; and
one or more silicone-based layers applied to the metallic wire; and
positioning a one-way passive valve in the cavity of the shunt tube.

12. The method of claim 11, wherein the attaching step comprises:
fabricating a shape memory alloy wire or mesh structure;
thermally configuring the shape memory alloy wire or mesh structure to expand outwardly from the exterior surface of the shunt tube for preventing migration of the shunting device; and
employing a mechanism for connecting the shape memory alloy wire or mesh structure configured to the shunt tube.

13. The method of claim 11, further comprising:
introducing the shunting device in-utero through the skull and into the brain of the fetus, such that the first end of the shunt tube is positioned in the skull and the opposite second end of the shunt tube is positioned in an amniotic sac outside of the skull;
allowing cerebrospinal fluid in the brain to flow into the first end and through the shunt tube;
pushing outward the flow of cerebrospinal fluid through the one-way passive valve of the shunt tube; and
discharging the cerebrospinal fluid through the opposite second end of the tube into the amniotic sac.

14. A method of preparing a ventriculoamniotic shunting in fetal isolated aqueductal stenosis, comprising:
pre-forming a metallic wire in a helical shape to form a helical-shaped wire;
applying one or more silicone-based layers to the helical-shaped wire to form a composite tube, comprising:
an exterior surface;
an interior surface;
a cavity formed by the interior surface;
a first end configured to be positioned inside a skull of a fetus;
an opposite second end configured to be positioned outside the skull of a fetus,
a length extending between the first and second ends;
at least two self-expanding anchors formed on the exterior surface along the length of the shunt tube, the at least two self-expanding anchors comprising a shape memory alloy wire or mesh structure, positioned in series, comprising:
a self-expanding first anchor configured to be positioned inside the skull of a fetus; and
a self-expanding second anchor configured to be positioned outside the skull of a fetus;
a bend in an elbow shape or angle from about 90 degrees to about 120 degrees forming an apex in length of the shunt tube and the apex of the bend positioned between the first anchor and the second anchor;
an inner diameter; and
an outer diameter; and
positioning a one-way passive valve in the cavity of the shunt tube.

15. The method of claim 14, wherein the applying step comprises dip coating and gravitational drying.

16. The device of claim 1, wherein the apex of the bend positioned between the first anchor and the second anchor is configured to be positioned adjacent the skull of the fetus.

17. The method of claim 11, wherein the apex of the bend positioned between the first anchor and the second anchor is configured to be positioned adjacent the skull of the fetus.

18. The method of claim 14, wherein the apex of the bend positioned between the first anchor and the second anchor is configured to be positioned adjacent the skull of the fetus.

* * * * *